United States Patent
Devereux

(10) Patent No.: US 12,096,739 B2
(45) Date of Patent: Sep. 24, 2024

(54) HYDRANGEA PLANT 'HMOPICO04-0'

(71) Applicant: James Devereux, Fort Collins, CO (US)

(72) Inventor: James Devereux, Fort Collins, CO (US)

( * ) Notice: Subject to any disclaimer, the term of this patent is extended or adjusted under 35 U.S.C. 154(b) by 0 days.

(21) Appl. No.: 17/401,099

(22) Filed: Aug. 12, 2021

(65) Prior Publication Data

US 2023/0067366 A1    Mar. 2, 2023

(51) Int. Cl.
*A01H 5/00* (2018.01)
*A01H 5/02* (2018.01)
*A01H 6/48* (2018.01)

(52) U.S. Cl.
CPC .................. *A01H 6/48* (2018.05); *A01H 5/02* (2013.01)

(58) Field of Classification Search
CPC ..................................... A01H 6/48; A01H 5/02
USPC .................................. Plt./250; 800/260, 298
See application file for complete search history.

(56) References Cited

U.S. PATENT DOCUMENTS

PP23,800 P2 *   8/2013   Gray ..................... A01H 6/48
                                                  Plt./250

* cited by examiner

*Primary Examiner* — Karen M Redden
(74) *Attorney, Agent, or Firm* — Cassandra Bright

(57) ABSTRACT

The invention relates to the field of *Hydrangea*, specifically, the variety designated 'HMOPICO04-0'. The variety 'HMOPICO04-0' is characterized by its lack of vernalization requirement for induction and development of flowering, day-length neutral flowering, cold tolerance to USDA Zone 5 and lace-cap inflorescence having pink and white flowers. The present invention relates to plant parts, including cells and any propagative material of the new variety 'HMOPICO04-0', use of any of the plant parts for reproducing the new variety 'HMOPICO04-0'. The present invention relates to methods using any plant parts or progeny of 'HMOPICO04-0' for the purpose of deriving additional new *Hydrangea* varieties. The present invention relates to seed, plants and plant parts produced by crossing 'HMOPICO04-0' with any other *Hydrangea* variety or other plant. The present invention also relates to methods to produce new varieties of *Hydrangea oleracea* using the variety 'HMOPICO04-0' and applying plant breeding techniques.

8 Claims, 2 Drawing Sheets
(2 of 2 Drawing Sheet(s) Filed in Color)

HYDRANGEA PLANT 'HMOPICO04-0'

FIELD OF THE INVENTION

The present invention relates to a new variety of *Hydrangea* referred to as 'HMOPICO04-0' as well as to new, distinct and stable characteristics found in *Hydrangea*. The present invention relates to plants which have all of the morphological and physiological characteristics described herein, as well as plant parts which can be used to reproduce plants having the characteristics specific to *Hydrangea* referred to as 'HMOPICO04-0'. The present invention also relates to methods for producing these plants of *Hydrangea* exhibiting the characteristics described herein. Furthermore, the present invention relates to a method of producing progeny *Hydrangea* plants by crossing the *Hydrangea* referred to as 'HMOPICO04-0', as either the female or seed or male or pollen parent, with another *Hydrangea* plant, or 'HMOPICO04-0', and selecting progeny. The present invention also relates to methods to produce new varieties of *Hydrangea* using the variety 'HMOPICO04-0' in a breeding program.

BACKGROUND OF THE INVENTION

The present invention relates to a new, distinct and stable variety of *Hydrangea*, hereinafter referred to by the variety denomination 'HMOPICO04-0'. The new *Hydrangea* 'HMOPICO04-0' originated from a controlled breeding program in Santa Paula, CA.

*Hydrangea* belong to the family Hydrangeacea and is a Genus consisting of about 25 species which are native to the Western Hemisphere and Eastern Asia. *Hydrangea* are a widely distributed ornamental shrub or subshrub. Extensive breeding programs exist for *Hydrangea* worldwide. Methods for propagation are well known and include terminal vegetative cuttings.

*Hydrangea* is one of the most important Genus of commercial flowering ornamental plants. Hundreds of varieties, both patented and unpatented are available to the public. Demand for and supply of *Hydrangea* plants has increased significantly in the last 20 years in the commercial horticulture market. Ornamental breeders seek to improve upon known characteristics as well as develop new and useful features.

When grown for ornamental horticulture, vernalization is required to induce flowering in *Hydrangea* plants. This process adds significantly to the cost and time of commercial plant production. It is the objective of the breeder to create efficiencies with improved varieties, both in terms of financial crop inputs and total crop time.

The current market of *Hydrangea* varieties all require vernalization in order to be brought into bloom. Significant efficiency can be realized by eliminating this step for the commercial grower.

Most known commercial varieties of *Hydrangea* bloom under long day conditions. As consumers prefer to buy flowering plants, this limits the sales period to Spring and Summer, unless artificial light conditions are provided to plants.

The new variety eliminates the need for vernalization. This represents significant potential to reduced propagative inputs for growers as well a shorter period of time to bring a plant into bloom. The day-length neutral characteristic increases the sales season, without the need to manipulate photoperiod.

Objectives of breeding programs are defined by the problems and weaknesses of the current cultivars. Crossing and selection have been made to improve flowering induction characteristics in *Hydrangea*. The variety described herein is an ornamental *Hydrangea* plant, having the above-mentioned improvements combined with attractive ornamental characteristics. Plants retain the desirable ornamental traits of *Hydrangea*, including large, colorful inflorescences, remontant flowering, together with novel and improved floral induction.

To those trained in the art, the improvements described herein are both valuable and quantitative assets.

SUMMARY OF THE INVENTION

The following embodiments and aspects thereof are described in conjunction with systems, tools and methods which are meant to be exemplary, not limiting in scope.

The present invention provides *Hydrangea* plant selections exhibiting no need for vernalization to begin flowering. Additionally, plants of 'HMOPICO04-0' begin flowering under any day-length, being day-length neutral. Plants of *Hydrangea* 'HMOPICO04-0' are hardy to USDA Zone 5. These qualities, combined with the description included herein, distinguish the new cultivar from known *Hydrangea* varieties.

These and other improvement and objectives have been achieved in accordance with the present invention which provide 'HMOPICO04-0' as a new *Hydrangea* cultivar that is the product of a planned breeding program conducted by the inventor in Santa Paula, CA.

The new variety 'HMOPICO04-0' can be produced by asexual reproduction to produce a population of progeny plants, each of which has the combination of characteristics as herein disclosed for the new variety 'HMOPICO04-0'.

Definitions

Terminology below may be useful for description and understanding of the new invention.
- Day-Length: A common term referring to the hours of daylight required to induce and develop flowering. Syn. photoperiodism.
- Day-Length Neutral: A flowering condition in which neither short nor long days are required to induce and develop flowering.
- Dormant: Temporarily inactive.
- First Node: The first growth zone above the roots on the stem.
- Hortensia: A common name in usage for *Hydrangea*
- Morphology: Form and structure.
- Node: Growth zone.
- Plant form: Overall structure and shape of the plant.
- Progeny: Off-spring or descendants.
- Vernalization: The cooling of plant material in order to induce flowering.

Additional Terminology, Related to Polyploidy

Euploids—polyploids with exact multiples of the complete set of chromosomes specific to a species. Haploid or Monoploid (one set; 1x), Diploid (two sets; 2x), Triploid (three sets; 3x), Tetraploid (four sets; 4x), Pentaploid (five sets; 5x), Hexaploid (six sets; 6x), Octaploid (eight sets; 8x), Decaploid (ten sets; 10x), Dodecaploid (12 sets; 12x).

Autopolyploids—polyploids with multiple chromosome sets derived from a single species—usually derived from chromosome doubling.

Allopolyploids—polyploids whose chromosomes are derived from different species. are a combination of genomes of different species (Acquaah 2007) due to hybridisation of two or more genomes followed by chromosome doubling or by the fusion of unreduced gametes between species (Acquaah 2007; Chen 2010; Jones et al. 2008; Ramsey and Schemske 1998). Can occur naturally or artificially Aneuploids—polyploids that contain either an addition or deletion of one or more specific chromosome(s) to the total number of chromosomes that usually make up the ploidy of a species (Acquaah 2007; Ramsey and Schemske 1998). Aneuploids are formed due to the formation of univalents and multivalents during meiosis of euploids

DEPOSIT INFORMATION

Appropriate biological material of *Hydrangea* plant named "HMOPICO04-0' was deposited and accepted on Apr. 5, 2024 at Bigelow National Center for Marine Algae & Microbiota, 60 Bigelow Drive, East Boothbay, ME 04544, a Budapest Treaty recognized depository which affords permanence of the deposit, and accorded International Depositary Authority Accession No. 202404010. During the pendency of the patent application access to the deposited biological material will be allowed to those persons properly designated by the Commissioner of Patents and Trademarks; that the deposited biological material will be replaced should it die or be destroyed during the enforceable life of any patent issued out of this patent application, for five years after the last request for a sample of the deposited biological material or for thirty years, whichever is longer; that upon issuance of a patent, Applicants will irrevocably remove all restrictions to access to the biological material; and that maintenance charges for the duration of the deposit will be paid

BRIEF DESCRIPTION OF THE DRAWINGS

The patent or application file contains multiple drawings executed in color. Copies of this patent or patent application publication with color drawing will be provided by the Office upon request and payment of the necessary fees.

The accompanying photographs illustrate the overall appearance and morphology of the new *Hydrangea* 'HMOPICO04-0' showing the colors as true as is reasonably possible with colored reproductions of this type. Colors in the photograph may differ slightly from the color values cited in the detailed botanical description which accurately describes the color of 'HMOPICO04-0'.

OBJECTS OF THE INVENTION

Figure 1:
FIG. 1 illustrates a side view of plants of *Hydrangea* 'HMOPICO04-0' at approximately 26 to 28 weeks of age. This photo was taken in Santa Paula, CA.
Figure 2:
FIG. 2 illustrates a close-up view of flowers of *Hydrangea* 'HMOPICO04-0'

The following embodiments and aspects thereof are described in conjunction with system, tools and methods which are meant to be exemplary, not limiting in scope The present invention relates to *Hydrangea* plants, and parts thereof, having all the physiological and morphological characteristics of *Hydrangea* 'HMOPICO04-0'.

Another embodiment relates to a plant produced by vegetative means which are *Hydrangea* 'HMOPICO04-0'. The present invention also relates to plant parts, such as pollen, seeds or inflorescence produced by *Hydrangea* 'HMOPICO04-0'.

Another embodiment relates to a method of producing seed which are *Hydrangea* 'HMOPICO04-0'.

Another embodiment also relates to a method of producing *Hydrangea* progeny comprising the steps of (a) self-pollinating *Hydrangea* 'HMOPICO04-0' (b) harvesting seeds produced from said self-pollination; and (c) producing plants from said harvested seeds.

The present invention also relates to producing progeny plants from the cross of *Hydrangea* 'HMOPICO04-0', as the female or male parent, with another *Hydrangea* plant, and selecting progeny plants from this cross.

The present invention also relates to producing progeny plants of *Hydrangea* 'HMOPICO04-0', by any known means of vegetative propagation.

The present invention also relates to producing progeny plants from *Hydrangea* 'HMOPICO04-0', from natural or induced mutation.

Another embodiment relates to tissue culture produced from protoplast of cells from *Hydrangea* 'HMOPICO04-0' plants disclosed in the subject application, wherein said cells or protoplasts are produced from a plant part selected from the group consisting of pollen, ovules, embryos, protoplasts, meristematic cells, callus, leaves, anthers, cotyledons, hypocotyl, pistils, roots, root tips, flowers, seeds, petiole and stems.

Another embodiment relates to a plant or a part thereof, produced by growing *Hydrangea* 'HMOPICO04-0', wherein the plant part comprises at least one cell of *Hydrangea* 'HMOPICO04-0'.

Another embodiment relates to tissue or cell culture of regenerable cells produced from the plants of *Hydrangea* 'HMOPICO04-0' as well as an *Hydrangea* plant regenerated from the tissue or cell culture of *Hydrangea* 'HMOPICO04-0'.

Another embodiment relates to a method of vegetatively propagating the plant of *Hydrangea* 'HMOPICO04-0', comprising the steps of: collecting tissue or cells capable of being propagated from a plant of *Hydrangea* 'HMOPICO04-0'; cultivating said tissue or cells to obtain proliferated shoots; and rooted said shoots to obtain rooted plantlets; or cultivating said tissue or cells to obtain shoots or to obtain plantlets and a plant produced by growing the plantlets or shoots of said plant.

A further embodiment relates to a method for developing an *Hydrangea* plant in an *Hydrangea* breeding program, comprising applying plant breeding techniques comprising crossing, recurrent selection, mutation breeding, wherein said mutation breeding selects for a mutation that is spontaneous or artificially induced, backcrossing, pedigree breeding, marker enhanced selection, haploid/double haploid production, ploidy manipulation, or transformation to the *Hydrangea* plant of *Hydrangea* 'HMOPICO04-0', or its parts, wherein application of said techniques results in development of an *Hydrangea* plant.

A further embodiment relates to a method of introducing a mutation into the genome of *Hydrangea* 'HMOPICO04-0', and wherein the resulting plant comprises at least one genome mutation and producing plants there from.

In addition to the exemplary aspects and embodiments described above, further aspects and embodiments will become apparent by study of the following descriptions.

BRIEF DESCRIPTION OF THE INVENTION

This invention is directed to *Hydrangea* plants having all the morphological and physiological characteristics of the variety 'HMOPICO04-0' produced from either vegetative cuttings or tissue culture.

The new *Hydrangea* 'HMOPICO04-0' can be produced by asexually reproducing progeny. Asexual reproduction of the new cultivar by vegetative means was first performed by vegetative cuttings during May of 2018, in Santa Paula, CA The first 'HMOPICO04-0' plants propagated through the use of such cuttings are maintained in Santa Paula, CA and have reproduced multiple generations. Subsequent asexual reproduction has demonstrated that the new cultivar reproduces true-to-type and that the combination of characteristics as herein disclosed for the new cultivar are firmly fixed and retained through successive generations of asexual reproduction.

The following traits have been repeatedly observed and are determined to be unique characteristics of 'HMOPICO04-0' which in combination distinguish these *Hydrangea* as new and distinct cultivars:
1. No vernalization required for induction and development of flowering.
2. Flowering is day length neutral and remontant.
3. Cold tolerant to USDA Zone 5.
4. Lace-cap inflorescence having pink and white sterile flowers and pink fertile flowers.

The new *Hydrangea* 'HMOPICO04-0' can be compared to *Hydrangea macrophylla* 'PIIHM-I' U.S. Pat. No. 20,176. Plants of 'PIIHM-I' differ from plants of 'HMOPICO04-0' in the following:
1. 'HMOPICO04-0' has no chill/vernalization requirement as does this comparator.
2. The new variety has pink and white sterile and fertile flowers; this comparator has pink flowers.
3. 'HMOPICO04-0', has stronger branches than this comparator.
4. 'HMOPICO04-0' has narrower foliage than this comparator.

*Hydrangea* 'HMOPICO04-0' can also be compared to the unpatented *Hydrangea macrophylla* 'BAILMER', U.S. Pat. No. 15,298. Plants of 'BAILMER' differ from plants of 'HMOPICO04-0' in the following:
1. 'HMOPICO04-0' has no chill/vernalization requirement as does this comparator.
2. The new variety has pink and white lace-cap inflorescences; this comparator has blue mop head inflorescences.
3. 'HMOPICO04-0', has stronger branches than this comparator.
4. 'HMOPICO04-0' has narrower foliage than this comparator.

'HMOPICO04-0' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant.

For example, substantial differences in plant height and diameter can be observed, depending upon environmental conditions and planting density. Inflorescence size and color can vary as well.

Detailed Botanical Description

The aforementioned drawings, together with the following observations, measurements and values describe the new *Hydrangea* 'HMOPICO04-0' as grown in a greenhouse in Santa Paula, CA Plants of 'HMOPICO04-0' were grown in a research greenhouse with temperatures ranging from approximately 5° C. to 18° C. during the day and night temperatures ranging from approximately 20° C. to 30° C. in the day and approximately 15° C. to 25° C. in the day. No artificial lighting or photoperiodic treatments were conducted. Plants were measured at approximately 4.5 months old from an unrooted cutting.

Color reference are made to the Royal Horticultural Society Colour Chart (RHS), 2007 edition, except where general colors of ordinary significance are used. Color values were taken under daylight conditions in a greenhouse in Ventura County, CA Plant Plant type: Flowering deciduous perennial shrub.
Age of Plant Described: Approximately 4.5 months from an unrooted cutting.
Growth Habit: Broadly rounded.
Height: 50 cm.
Plant Spread: 65 cm.
Plant vigor: Moderate.
Branching Habit: Strong branching from a pinch. Branches occurring at mostly obtuse angles.
Length of Primary Lateral Branches: Average range 30 to 45 cm.
Diameter of Lateral Branches: 4 to 6 mm.
Quantity of Lateral Branches: Average range 15 to 25.
Stem:
    Stem shape: Round.
    Stem strength: Strong.
    Color:
        Immature: RHS Yellow-Green 147A. flushed Greyed-Purple 187A.
        Mature: RHS Yellow-Green 144A.
    Texture: Glabrous.
    Aspect. Straight, occurring at 15° to 5° from center.
Internode length: 5.5 to 6.5 cm.

Foliage

Leaf:
    Arrangement: Opposite.
    Leaf shape: Elliptic.
    Average Length: 5 to 9 cm.
    Average Width: 2.8 to 3.5 cm.
    Apex: Acuminate.
    Base: Obtuse.
    Margin: Dentate.
    Texture of top surface: Glabrous.
    Texture of bottom surface: Glabrous.
    Color:
        Young foliage upper side: Near Green 137B, flushed Greyed-Purple 187A. Margin flushed Greyed-Purple N187A.

Young foliage under side: Near Green 138B, flushed
    Greyed-Purple 187A. Margin flushed Greyed-Purple
    N187A.
Mature foliage upper side: RHS Green 137A
Mature foliage under side: RHS Green 137C.
Venation:
    Pattern: Pinnate.
    Color upper side: RHS Yellow-Green 144C.
    Color under side: RHS Yellow-Green 145A.
Petiole:
    Average Length: Average 1.8 cm.
    Diameter: 3 mm to 4 mm.
    Petiole color upper side:
        Young foliage RHS Yellow-Green 146B.
        Mature foliage: RHS Yellow-Green 146B, edges
            flushed Greyed-Purple N186A.
    Petiole color lower side:
        Young foliage Yellow-Green 146B
        Mature foliage: RHS Yellow-Green 146B, flushed
            Greyed-Purple N186C.
    Petiole Texture upper side: Glabrous.
    Petiole Texture lower side: Glabrous.

Flower

Natural flowering season: Day length neutral, flowering
    begins approximately 13 to 16 weeks after planting during
    any time of the year without chill hours.
Inflorescence:
    Type: Lacecap. Compound umbel.
    Quantity of flowers per inflorescence:
        Fertile flowers: 400-500.
        Sterile flowers: Average 25.
    Shape: Flattened disc.
    Height: About 8 to 12 cm.
    Diameter: 12 cm to 25 cm.
    Fragrance: None detected.
Sterile Flower:
    Bud shape: Round.
    Bud length: 9 mm.
    Bud diameter: 8 mm.
    Bud color: Near RHS White N155C, margins flushed Red
        52B.
    Aspect: Upright. Aging flowers somewhat pendulous.
    Flower depth: 7 mm.
    Flower Diameter: 4 to 6 cm.
    Persistence: Self-cleaning.
Sterile Flower Petals: Petals do not develop/open, or not
    present.
Sterile Flower Sepal:
    Arrangement. Cruciform, strongly overlapping.
    Number: 4.
    Shape: Wide deltate to irregular orbicular.
    Tip: Broad acute.
    Base: Obtuse.
    Margin: Entire.
    Length: 2.2 to 3.4 cm.
    Width: 3 to 4 cm.
    Texture, Upper: Smooth.
    Texture, Lower: Smooth.
    Color:
        Upper surface at first opening: Near RHS White
            N155C, margins flushed Red-Purple 63C, margin
            63A.
        Under surface at first opening: Near RHS White
            N155C, margin 63A.
        Upper surface at maturity: Near RHS White N155C,
            margins lightly flushed Red-Purple 63C, margin
            63A.
        Under surface at maturity: Near RHS White N155C,
            margin 63B.
Sterile Flower Pedicel:
    Length: 2.5 cm to 3.3 cm.
    Diameter: 2.5 mm.
    Angle: About 90°, pedicel strongly curved.
    Strength: Flexible.
    Texture: Glabrous.
    Color: Immature near RHS Red 49C; Mature near Red-
        Purple 63D.
Fertile Flower: Rotate flower composed of petals and notice-
    ably protruding stamens. Petals do not unfurl on all
    flowers. Approximately 50% of flowers remain with
    furled petals and protruding stamens.
    Bud shape: Sphere
    Bud length: 3 mm.
    Bud diameter: 2 mm.
    Bud color: Near Red-Purple 64B.
    Flower aspect: Upright.
    Flower shape: Rotate.
    Flower diameter: 6 mm, petals only when fully unfurled;
        including protruding stamens 8 mm.
    Flower length: 4 mm petals only; including protruding
        stamens 6 mm
    Persistence: Self-cleaning.
Fertile Flower Petals:
    Arrangement: Rotate.
    Quantity: 5.
    Length of petal: 2 mm.
    Width of petal: 1 mm to 2 mm.
    Apex: Acute.
    Shape of petal: Narrowly elliptic.
    Petal margin: Entire.
    Petal base: Truncate.
    Petal Texture: Smooth, upper and under side.
    Color:
        Upper surface at first opening: Near Red-Purple 64B.
        Under surface at first opening: Near Red-Purple 64B.
        Upper surface at maturity: Near Red-Purple 64A.
        Under surface at maturity: Near Red-Purple 64A.
Fertile Flower Sepal: Minute and inconspicuous, less than
    0.5 mm, colored near Red-Purple 64B.
Fertile Flower Pedicel:
    Angle: About 45°.
    Strength: Flexible.
    Length: Average 5 mm.
    Width: 1 mm.
    Texture: Glabrous.
    Color: Near RHS Yellow-Green 146C flushed Red-Purple
        63A.

Reproductive Organs

Sterile flowers: Androecium irregularly present. Somewhat
    mis-formed gynoecium irregularly present.
Stamens:
    Number: 1 to 8.
    Filament length: 5 mm.
    Filament color. RHS Red-Purple 63C.
Anthers:
    Shape: Globular.
    Length: 1 mm.
    Color: RHS Greyed-Orange 163B.
    Pollen color: Not observed.

Pistil:
    Number: 3.
    Length: 1 to 3 mm.
    Style:
        Length: 1 to 3 mm.
        Color: Near Red-Purple 65C.
    Ovary: About 0.5 mm in diameter and length. Colored near Red-Purple 63D
    Stigma:
        Shape: Bi-lobed.
        Color: Near Red-Purple 65A.
Fertile flowers:
Stamens:
    Number: About 10.
    Filament length: 5 mm to 9 mm.
    Filament color: RHS Red-Purple 65D.
Anthers:
    Shape: Globular.
    Length: 1 mm.
    Color: RHS Yellow-Green 146D.
    Pollen color. RHS Yellow-White 158D.
    Pollen amount. Moderate.
Pistil:
    Number: 3.
    Length: 2 mm to 3 mm.
    Style:
        Length: 1 mm to 2 mm.
        Color: Near Red-Purple 65D.
    Ovary color: Near Red-Purple 65D.
    Stigma:
        Shape: Bi-lobed.
        Color: Near Red-Purple 63A.

Other Characteristics

Seeds and fruits: Not observed to date.
Disease/pest resistance: Neither resistance nor susceptibility to normal diseases and pests of *Hydrangea* have been observed.
Temperature tolerance: Low temperature tolerant to USDA Zones 5.

I claim:

1. *Hydrangea* 'HMOPICO04-0', representative biological material deposited at Bigelow Laboratory for Ocean Sciences, East Boothbay, ME under Accession number 202404010.

2. A plant or a plant part thereof produced by growing the plant of claim 1, wherein the plant or plant part comprises at least one cell of *Hydrangea* 'HMOPICO04-0'.

3. A *Hydrangea* plant or part thereof, having the physiological and morphological characteristics of the plants of claim 1.

4. The tissue or cell culture of regenerable cells produced from the plant of claim 1.

5. The tissue or cell culture of claim 4, comprising tissues or cells from a plant part selected from the group consisting of leaves, vegetative cuttings, pollen, embryos, cotyledons, hypocotyl, meristematic cells, roots, root tips, pistils, anthers, flowers and stems.

6. A method of producing *Hydrangea* progeny comprising the steps of (a) crossing a plant of *Hydrangea* 'HMOPICO04-0' as a female or male parent with another *Hydrangea* plant or other plant and (b) selecting progeny, representative biological material of *Hydrangea* 'HMOPICO04-0' has been deposited at Bigelow Laboratory for Ocean Science, East Boothbay, ME, under Accession number 202404010.

7. The method according to claim 6, wherein the second plant is *Hydrangea* 'HMOPICO04-0'.

8. A method for developing a *Hydrangea* plant in a plant breeding program using plant breeding techniques, including crossing, recurrent selection, mutation breeding, wherein said mutation breeding selects for a mutation that is spontaneously or naturally induced or artificially induced, backcrossing, pedigree breeding, marker enhanced selection, haploid/double haploid production or transformation to a plant of *Hydrangea* 'HMOPICO04-0', or it's parts, or progeny wherein application of said techniques results in development of a *Hydrangea* plant, representative biological material of *Hydrangea* 'HMOPICO04-0' has been deposited at Bigelow Laboratory for Ocean Science, East Boothbay, ME, under Accession number 202404010.

\* \* \* \* \*